(12) United States Patent
May et al.

(10) Patent No.: US 10,271,879 B2
(45) Date of Patent: Apr. 30, 2019

(54) SURGICAL INSTRUMENT AND METHODS OF USE

(71) Applicant: Warsaw Orthopedic, Inc., Warsaw, IN (US)

(72) Inventors: Jason M. May, Cordova, TN (US); Joshua W. Simpson, Collierville, TN (US); William Allan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 307 days.

(21) Appl. No.: 14/854,967

(22) Filed: Sep. 15, 2015

(65) Prior Publication Data

US 2017/0071640 A1    Mar. 16, 2017

(51) Int. Cl.
| | | |
|---|---|---|
| *A61B 17/58* | (2006.01) |
| *A61B 17/60* | (2006.01) |
| *A61F 2/00* | (2006.01) |
| *A61B 17/70* | (2006.01) |
| *A61B 17/88* | (2006.01) |

(52) U.S. Cl.
CPC ...... *A61B 17/7082* (2013.01); *A61B 17/7077* (2013.01); *A61B 17/8888* (2013.01)

(58) Field of Classification Search
CPC combination set(s) only.
See application file for complete search history.

(56) References Cited

U.S. PATENT DOCUMENTS 5,291,811 A * 3/1994 Goss ............... B25B 13/065
                                                              411/404
8,403,957 B2 * 3/2013 Martinek ........... A61B 17/0401
                                                              606/232

* cited by examiner

*Primary Examiner* — Sameh Boles (57) ABSTRACT

A surgical instrument includes a member defining a longitudinal axis and including an engagement portion. The engagement portion includes at least one element engageable with an implant fastener. The at least one element includes a drive interface and an arcuate surface spaced from the drive interface. The arcuate surface includes at least one interference point engageable with the implant fastener. Implants, systems, constructs and methods are disclosed.

20 Claims, 4 Drawing Sheets

SURGICAL INSTRUMENT AND METHODS OF USE

TECHNICAL FIELD

The present disclosure generally relates to medical devices for the treatment of musculoskeletal disorders, and more particularly to a surgical system for delivering and/or fastening implants with a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. Surgical instruments are employed, for example, to engage the fasteners for attachment to the exterior of two or more vertebral members. This disclosure describes an improvement over these prior technologies.

SUMMARY

In one embodiment, a surgical instrument is provided. The surgical instrument includes a member defining a longitudinal axis and including an engagement portion. The engagement portion includes at least one element engageable with an implant fastener. The at least one element includes a drive interface and an arcuate surface spaced from the drive interface. The arcuate surface includes at least one interference point engageable with the implant fastener. In some embodiments, systems, implants, constructs and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system are discussed in terms of medical devices for the treatment of musculoskeletal disorders and more particularly, in terms of a surgical system for delivering and/or fastening implants with a surgical site and a method for treating a spine. In some embodiments, the surgical system includes a surgical instrument, such as, for example, an implant driver. In some embodiments, the surgical instrument includes a screw driver having a tip geometry that resists and/or prevents toggle.

In some embodiments, the surgical system comprises a surgical instrument having a zero toggle/self-retaining bone screw drive interface. In some embodiments, the surgical system comprises a surgical instrument including a driver that secures a fastener, such as, for example, a bone screw to the driver and provides a zero toggle interface. In some embodiments, the surgical system comprises a surgical instrument including a zero toggle driver interface, which fully engages along a driving face and a single point contact on a trailing edge of the drive that provides zero toggle. In some embodiments, the surgical system comprises a surgical instrument including a single point interface that allows the driver to be removed from a bone screw with low force. In some embodiments, the surgical system comprises a surgical instrument including a single line contact interface that allows the driver to be removed from a bone screw with low force. In some embodiments, the surgical system comprises a surgical instrument including a driver interface, which fully contacts on a loaded edge during bone screw insertion and point contact on the trailing edge for zero toggle. In some embodiments, the surgical system comprises a surgical instrument including a robust zero toggle driver.

In some embodiments, the surgical system comprises a self-retaining/zero toggle driver interface. In some embodiments, the interface includes a flute run-out that creates interference on a backside of the driver, for example, as the driver is rotated clockwise for tightening. In some embodiments, the interface engages a bone screw at a full driving surface and a point on a trailing edge of each flute. In some embodiments, the surgical system comprises a spline driver.

In some embodiments, the surgical system comprises a self-retaining/zero toggle driver interface that allows for engagement with a six-point torx engagement surface/hexalobular drive, which includes an undercut region and a lobe. In some embodiments, the drive interface is machined in a 12-point engagement surface/drive. In some embodiments, the engagement surface/drive is formed with a method that includes machine cutting, and in some embodiments, the cutting step is repeated to form an engagement surface/drive pattern such that the cuts overlap to form one or a plurality of undercut regions. In some embodiments, the method includes the step of forming an engagement surface/drive pattern such that the pattern includes one or a plurality of lobes.

In some embodiments, the surgical system may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context dearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, spinal implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system 10 including a surgical instrument, such as, for example, a surgical implant driver 12, and a fastener, such as, for example, a bone screw 14.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®, ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with an open or mini-open, minimal access and/or minimally invasive including percutaneous surgical technique to deliver and fasten an implant, such as, for example, bone screw 14 at a surgical site within a body of a patient, for example, a section of a spine. In some embodiments, the components of surgical system 10 are configured to fix a spinal rod, connector and/or plate to a spine via a bone fastener for a surgical treatment to treat various spine pathologies, such as those described herein.

Figure 1:
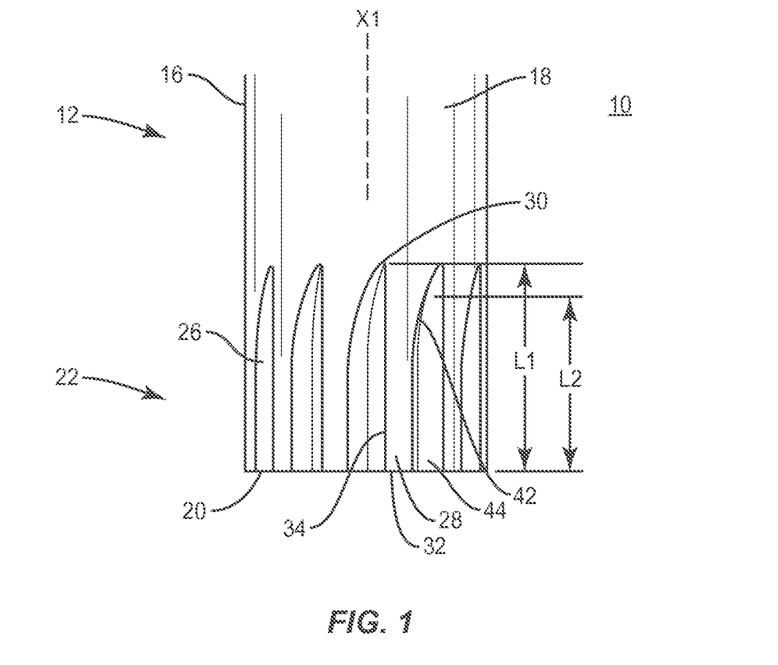
FIG. 1 is a side break away view of components of one embodiment of a spinal implant system in accordance with the principles of the present disclosure.
Figure 2:
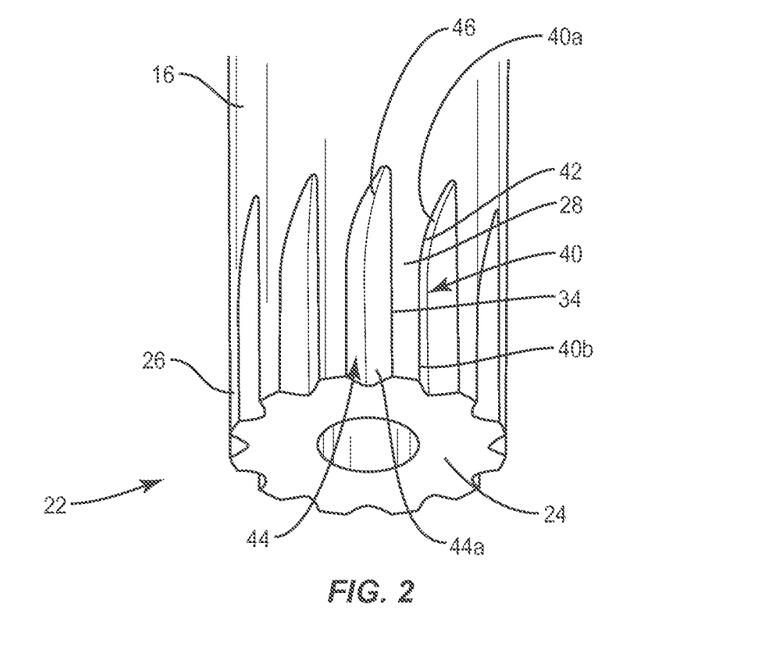
FIG. 2 is a perspective view of the components shown in FIG. 1.

Driver 12 includes a member, such as, for example, an elongated shaft 16. Shaft 16 extends between an end, such as, for example, a proximal end 18 and an end, such as, for example, a distal end 20. In some embodiments, end 18 is configured for engagement and connection with a handle (not shown), which is configured to facilitate manipulation of driver 12. In some embodiments, the handle may be disposed at alternate orientations relative to shaft 16, such as, for example, transverse, perpendicular and/or other angular orientations such as acute or obtuse. In some embodiments, end 18 is configured for engagement and connection with an adaptor, extension and/or other connection to facilitate manipulation of driver 12.

In some embodiments, end 18 includes a tool engagement surface (not shown) configured to engage an actuator, such as, for example, a surgical instrument and/or hand drill to rotate end 20 in a first direction and/or an opposing second direction, such as, for example, clockwise and counterclockwise directions. In some embodiments, end 18 may include an interchangeable driving handle removably connected to end 18 such that torque applied manually or by a motorized actuator to the handle is transmitted to shaft 16.

In some embodiments, end 18 is configured to engage an actuator, such as, for example, a motorized actuator, such as, for example, a powered drill (not shown). In some embodiments, the motorized actuator includes a mating connector, such as, for example, a chuck. In some embodiments, the chuck includes a socket that is configured to mate with end 18. In some embodiments, the motorized actuator includes an electric motor, such as, for example, an electric drill motor that is connected to a power source, such as, for example, a battery and/or AC source, for rotating end 20. In one embodiment, the motorized actuator may be pneumatic or hydraulic.

End 20 includes an engagement portion 22. Portion 22 is configured for engagement with bone screw 14, as described herein. Shaft 16 has a cylindrical cross sectional configuration between ends 18, 20. In some embodiments, a portion of shaft 16 may have alternate cross section configurations, such as, for example, oval, oblong, triangular, square, polygonal, irregular, uniform, non-uniform, offset, staggered, and/or tapered. Shaft 16 defines a longitudinal axis X1.

Engagement portion 22 is configured to mate with a socket, as described herein, of bone screw 14. Engagement portion 22 includes a distal face 24. Distal face 24 includes a flat or even surface. In some embodiments, distal face 24 may have various surface configurations, such as, for example, rough, threaded, arcuate, undulating, porous, semi-porous, dimpled, polished and/or textured. Engagement portion 22 includes an outer surface 26 defining at least one element, such as, for example, a lobe 28. In some embodiments, engagement portion 22 includes one or a plurality of elements. In some embodiments, engagement portion 22 includes twelve (12) lobes 128.

Engagement portion 22 includes a plurality of spaced apart lobes 28 disposed circumferentially about engagement portion 22. Each lobe 28 extends between an end, such as, for example, a proximal end 30 and an end, such as, for example, a distal end 32. Lobe 28 defines a length L1 extending between ends 30, 32.

Lobe 28 includes a drive interface, such as, for example, a drive edge 34. Drive edge 34 extends between ends 30, 32, along and including the entire length L1. In some embodiments, drive edge 34 has a linear configuration. In some embodiments, all or portions of drive edge 34 may include various configurations and/or be disposed in various orientations, such as, for example, angular, arcuate, undulating, series, parallel, offset and/or staggered.

In some embodiments, extension of drive edge 34 along length L1 disposes the entire surface of drive edge 34 into contacting engagement with an interface surface of the surface that defines the socket of bone screw 14, as described herein, which rotates bone screw 14. In some embodiments, fully contacting engagement of the entire surface of drive edge 34 with the interface surface of the socket of bone screw 14 provides a configuration that resists and/or prevents toggle between driver 12 and bone screw 14. In some embodiments, this configuration provides zero toggle and a robust drive interface.

Lobe 28 includes a trailing edge 40 that is spaced apart from drive edge 34. Trailing edge 40 includes an arcuate surface 40a and a linear surface 40b. In some embodiments, all or portions of trailing edge 40 may include various configurations and/or be disposed in various orientations, such as, for example, angular, arcuate, undulating, series, parallel, offset and/or staggered.

Arcuate surface 40a includes an interference point 42 disposed along trailing edge 40. Interference point 42 is positioned at a length L2 along trailing edge 40 and measured from distal face 24. Interference point 42 engages an interface surface of the surface that defines the socket of bone screw 14, as described herein, to retain driver 12 with bone screw 14 in an interference fit. In some embodiments, the interference fit includes a pressure fit and/or friction fit. In some embodiments, arcuate surface 40a includes one or a plurality of interference points and/or surfaces.

In some embodiments, interference point 42 provides a single point contact on trailing edge 40 that resists and/or prevents toggle between driver 12 and bone screw 14, and a single point interface that allows driver 12 to be removed from bone screw 14 with relatively low force. In some embodiments, driver 12 includes a zero toggle/self-retaining bone screw drive interface, which is robust for engagement with bone screw 14.

The outer surface of engagement portion 22 defines grooves 44 disposed between lobes 28. Grooves 44 extend along length L1 and are disposed between edges 40, 34 of adjacent lobes 28, for example, a groove 44 is defined between a trailing edge 40 of a first lobe 28 and a drive edge 34 of a successive or trailing lobe 28.

In some embodiments, each groove 44 extends between a distal opening 44a disposed adjacent distal face 24 and a closed proximal surface, such as, for example, a flute run-out 46. In some embodiments, groove 44 tapers to form run-out 46. The surface that defines run-out 46 includes interference point 42 and has an arcuate configuration to facilitate retention of driver 12 with bone screw 14 in an interference fit. In some embodiments, driver 12 engages bone screw 14 with a self-retaining/zero toggle driver interface. In some embodiments, the interface of the surface that defines the socket of bone screw 14 and the surface that defines run-out 46 creates an interference fit on a side of driver 12, for example, as driver 12 is rotated clockwise for tightening. In some embodiments, the interfaces of driver 12 and bone screw 14 include engagement at drive edge 34 and at least interference point 42 on a trailing edge of run-our 46.

Bone screw 14 includes a shaft 50 configured to penetrate tissue, such as, for example, bone. Shaft 50 includes a thread form on an outer surface thereof. In some embodiments, the thread form may extend such that shaft 50 is threaded along the entire length thereof. In some embodiments, all or only a portion of shaft 50 may have various surface configurations, such as, for example, rough, threaded, arcuate, undulating, porous, semi-porous, dimpled, polished and/or textured.

Figure 3:
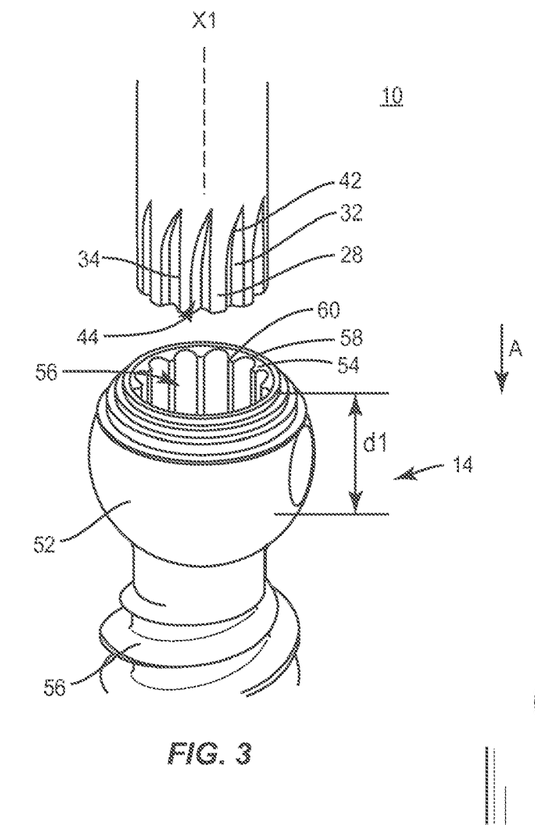
FIG. 3 is a perspective break away view of components of one embodiment of a spinal implant system in accordance with the principles of the present disclosure.
Figure 4:
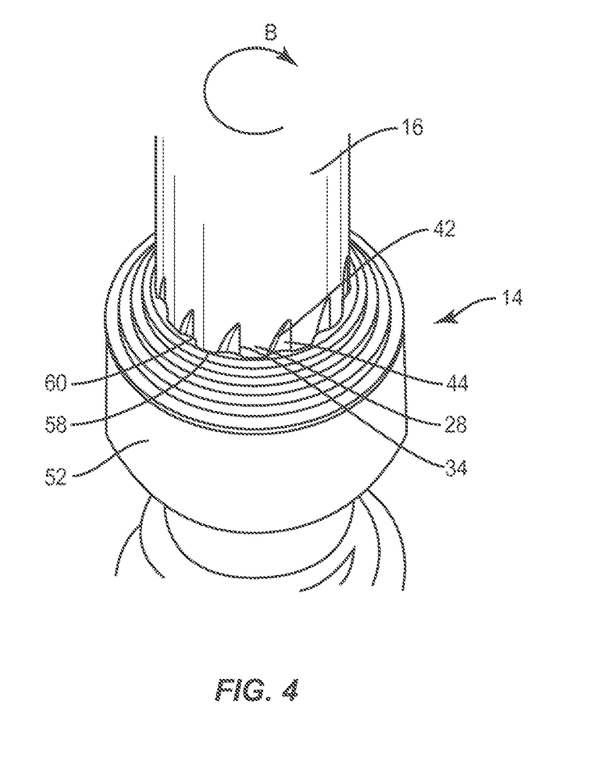
FIG. 4 is a break away view of the components shown in FIG. 3.

Bone screw 14 includes a head 52. Head 52 includes a surface 54. Surface 54 defines a socket 56. Socket 56 is configured for a mating engagement with engagement portion 22. Surface 54 defines recesses 58 configured for disposal of lobes 28. Surface 54 includes protrusions 60 configured for disposal within grooves 44. Socket 56 includes a depth dl dimensioned to receive engagement portion 22. In some embodiments, depth dl is equal to length L1. In some embodiments, depth dl is equal to length L2.

In operation, driver 12 is matingly engaged with surface 54 and disposed with socket 56 such that lobes 28 are disposed within recesses 58 and protrusions 60 are disposed within grooves 44. Drive edge 34 of a first lobe 28 fully engages a first side of a protrusion 60 to form a drive interface along the entire length L1 for engaging and rotating bone screw 14 in a selected direction, as described herein. Trailing edge 40 of a second, adjacent lobe 28 engages a second side of protrusion 60 such that interference point 42 forms an interface with the surface of the second side of protrusion 60 in an interference fit, as described herein, to retain bone screw 14 with driver 12.

In assembly, operation and use, surgical system 10, similar to surgical systems and methods described herein, is employed with a surgical procedure for treatment of a spinal disorder affecting a section of a spine of a patient, as discussed herein. For example, surgical system 10 can be used with a surgical procedure for treatment of a condition or injury of an affected section of the spine including vertebrae (not shown). In some embodiments, one or all of the components of surgical system 10 can be delivered or implanted as a pre-assembled device or can be assembled in situ. Surgical system 10 may be completely or partially revised, removed or replaced.

For example, surgical system 10 can be employed with a surgical treatment of an applicable condition or injury of an affected section of a spinal column and adjacent areas within a body, such as, for example, vertebrae. In some embodiments, surgical system 10 may be employed with one or a plurality of vertebra. To treat a selected section of the vertebrae, a medical practitioner obtains access to a surgical site including the vertebrae in any appropriate manner, such as through incision and retraction of tissues. In some embodiments, surgical system 10 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of surgical system 10. A preparation instrument (not shown) can be employed to prepare tissue surfaces of the vertebrae, as well as for aspiration and irrigation of a surgical region.

Pilot holes or the like are made in selected vertebra of the vertebrae for receiving bone screws 14. Surgical system 10 is disposed adjacent the vertebrae at a surgical site and the components of surgical system 10 including driver 12, are manipulable to drive, torque, insert or otherwise connect bone screws 14 to the vertebrae.

Driver 12 is translated axially relative to screw 14 along axis X1, in a direction shown by arrow A in FIG. 3, such that driver 12 is matingly engaged with surface 54 and disposed with socket 56. Lobes 28 are disposed within recesses 58 and protrusions 60 are disposed within grooves 44. Drive edge 34 of a first lobe 28 fully engages a first side of a protrusion 60 to form a drive interface along the entire length L1 for engaging and rotating bone screw 14 in a selected direction. Trailing edge 40 of a second, adjacent lobe 28 engages a second side of protrusion 60 such that interference point 42 forms an interface with the surface of the second side of protrusion 60 in an interference fit, as described herein, to retain bone screw 14 with driver 12.

Upon mating connection of driver 12 with bone screw 14, driver 12 is rotated, in a direction shown by arrow B in FIG. 4, such that rotation of driver 12 and the interface of driving edge 34 with the first side of protrusion 60 rotates bone screw 14 to provide a driving torque to fasten bone screw 14 with vertebrae. The interfaces of driver 12 with bone screw 14 resist and/or prevent toggle between driver 12 and bone screw 14, and include at least a single point interface that allows driver 12 to be removed from bone screw 14 with relatively low force.

Once access to the surgical site is obtained, the particular surgical procedure is performed. The components of surgical system 10, including bone screw 14 are employed to augment the surgical treatment. For example, bone screw 14 may be inserted into bone or other tissue with driver 12, for example, via clockwise or counterclockwise rotation. Bone screw 14 may be delivered, introduced, inserted and/or removed from bone or other tissue with driver 12.

Surgical system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, surgical system 10 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, such as, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implant components of surgical system 10 are removed from the surgical site and the incision is closed.

Figure 5:
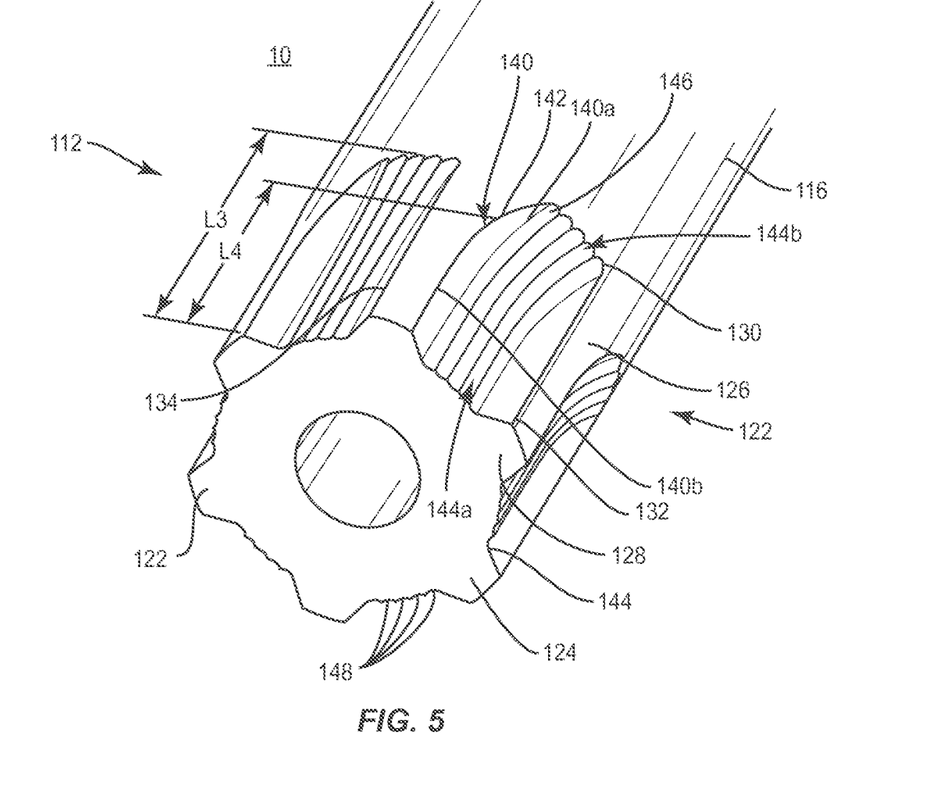
FIG. 5 is a perspective break away view of components of one embodiment of a spinal implant system in accordance with the principles of the present disclosure.
Figure 6:
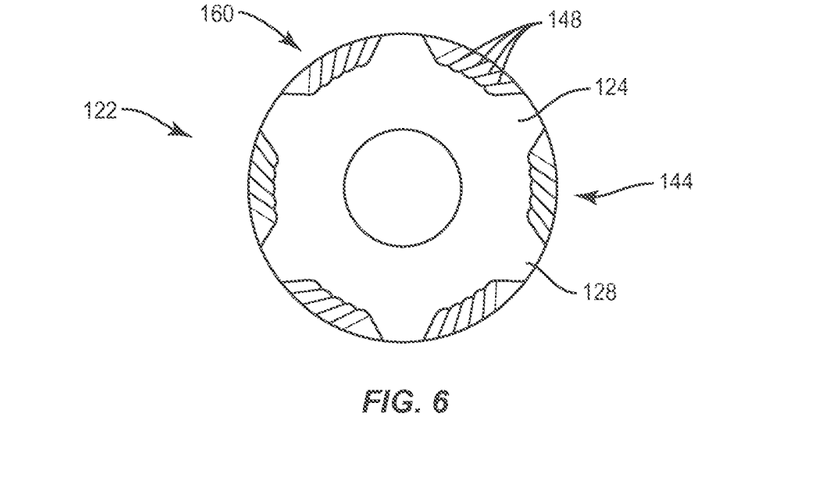
FIG. 6 is an end view of the components shown in FIG. 5.
Figure 7:
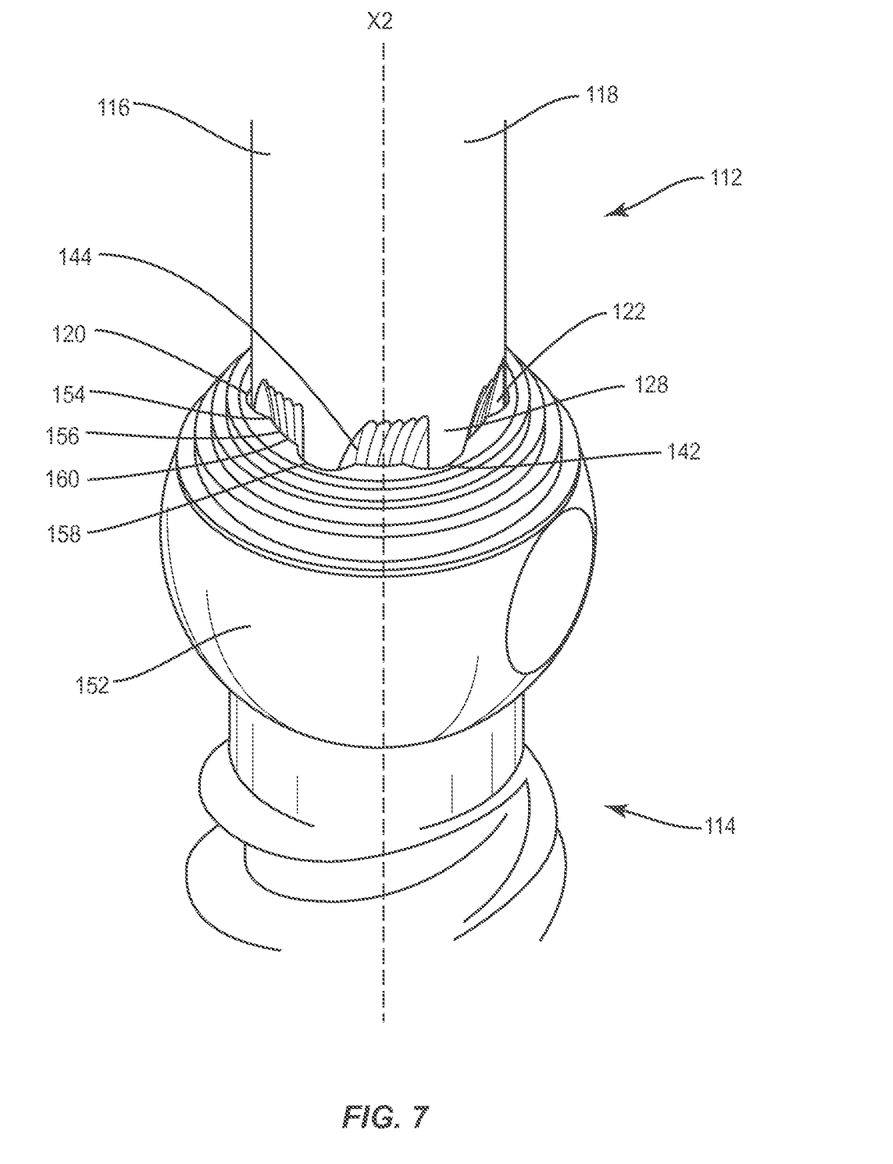
FIG. 7 is a perspective break away view of components of one embodiment of a spinal implant system in accordance with the principles of the present disclosure.

In one embodiment, as shown in FIGS. 5-7, surgical system 10, similar to the systems and methods described above with regard to FIGS. 1-4, includes a driver 112, similar to driver 12 described herein, and a bone screw 114, similar to bone screw 14 described herein.

Driver 112 includes an elongated shaft 116, similar to shaft 16 described herein, which extends between a proximal end 118 and a distal end 120. Shaft 116 defines a longitudinal axis X2. End 120 includes an engagement portion 122, similar to engagement portion 22 described herein.

Engagement portion 122 is configured to mate with a socket of bone screw 114. Engagement portion 122 includes a distal face 124. Engagement portion 122 includes an outer surface 126 defining a plurality of spaced apart lobes 128 disposed circumferentially about engagement portion 122. Each lobe 128 extends between a proximal end 130 and a distal end 132. Lobe 128 defines a length L3 extending between ends 130, 132. In some embodiments, portion 122 includes six lobes 128 forming a hexalobular drive.

Lobe 128 includes a drive interface, such as, for example, a drive edge 134, similar to drive edge 34 described herein. Drive edge 134 extends between ends 130, 132, along and including the entire length L3. In some embodiments, extension of drive edge 134 along length L3 disposes the entire surface of drive edge 134 into contacting engagement with an interface surface of the surface that defines the socket of bone screw 114, as described herein, which rotates bone screw 114. In some embodiments, fully contacting engagement of the entire surface of drive edge 134 with the interface surface of the socket of bone screw 114 provides a configuration that resists and/or prevents toggle between driver 112 and bone screw 114.

Lobe 128 includes a trailing edge 140, similar to trailing edge 40 described herein, which is spaced apart from drive edge 134. Trailing edge 140 includes an arcuate surface 140a and a linear surface 140b. Arcuate surface 140a includes an interference point 142, similar to interference point 142 described herein, disposed along trading edge 140. Interference point 142 is positioned at a length L4 along trailing edge 140 and measured from distal face 124. Interference point 142 engages an interface surface of the surface that defines the socket of bone screw 114, as described herein, to retain driver 112 with bone screw 114 in an interference fit. In some embodiments, interference point 142 provides a single point contact on trailing edge 140 that resists and/or prevents toggle between driver 112 and bone screw 114, and a single point interface that allows driver 112 to be removed from bone screw 114 with relatively low force. In some embodiments, driver 112 includes a zero toggle/self-retaining bone screw drive interface, which is robust for engagement with bone screw 114.

The outer surface of engagement portion 122 defines grooves 144, similar to grooves 44 described herein, disposed between lobes 128. Grooves 144 extend along length L3 and are disposed between edges 140, 134 of adjacent lobes 128, for example, a groove 144 is defined between a trailing edge 140 of a first lobe 128 and a drive edge 134 of a successive or trailing lobe 128.

In some embodiments, each groove 144 extends between a distal opening 144a disposed adjacent distal face 124 and a closed proximal surface 144b. Proximal surface 144b includes a flute run-out 146. The surface that defines run-out 146 includes interference point 142 and has an arcuate configuration to facilitate retention of driver 112 with bone screw 114 in an interference fit. Groove 144 includes a plurality of undercuts 148. In some embodiments, undercuts 148 are machine cut such that undercuts 148 overlap to form an undercut region 160. In some embodiments, as a machining process forms undercuts 148, a distance is passed over surface 126 to form lobes 128. In some embodiments, undercuts 148 comprise one or a plurality of ridges disposed between lobes 128.

In some embodiments, the interface of the surface that defines the socket of bone screw 114 and the surface that defines run-out 146 creates an interference fit on a side of driver 112, for example, as driver 112 is rotated clockwise for tightening. In some embodiments, the interfaces of driver 112 and bone screw 114 include engagement at drive edge 134 and at least interference point 142 on a trading edge of run-out 146.

Bone screw 114 includes a shaft 150 configured to penetrate tissue, such as, for example, bone. Bone screw 114 includes a head 152. Head 152 includes a surface 154. Surface 154 defines a socket 156. Socket 156 is configured for a mating engagement with engagement portion 122. Surface 154 defines recesses 158 configured for disposal of lobes 128. Surface 154 includes protrusions 160 configured for disposal within grooves 144. Socket 156 includes a depth dimensioned to receive engagement portion 122.

In operation, driver 112 is matingly engaged with surface 154 and disposed with socket 156 such that lobes 128 are disposed within recesses 158 and protrusions 160 are disposed within grooves 144. Drive edge 134 of a first lobe 128 fully engages a first side of a protrusion 160 to form a drive interface along the entire length L3 for engaging and rotating bone screw 114 in a selected direction, as described herein. Trailing edge 140 of a second, adjacent lobe 128 engages a second side of protrusion 160 such that interference point 142 forms an interface with the surface of the second side of protrusion 160 in an interference fit, as described herein, to retain bone screw 114 with driver 112.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a member defining a longitudinal axis and including an engagement portion, the engagement portion including at least one element engageable with an implant fastener, the at least one element including a drive edge and a trailing edge, the drive edge and the trailing edge defining a groove therebetween, the drive edge intersecting the trailing edge at a proximal tip of the groove, wherein the groove includes a distal portion defined by a first section of the drive edge and a first section of the trailing edge and a proximal portion defined by a second section of the drive edge and a second section of the trailing edge, wherein the first section of the drive edge, the first section of the trailing edge, and the second section of the drive edge each extend parallel to the longitudinal axis, wherein the second section of the trailing edge is arcuately curved from the first section of the trailing edge to the proximal tip, and wherein the second section of the trailing edge includes at least one interference point engageable with the implant fastener.

2. A surgical instrument as recited in claim 1, wherein the member includes an elongated shaft extending between a first end and a second end, the second end including the engagement portion.

3. A surgical instrument as recited in claim 1, wherein the at least one element includes a lobe.

4. A surgical instrument as recited in claim 1, wherein the at least one element includes 12 lobes.

5. A surgical instrument as recited in claim 1, wherein the at least one element includes a plurality of elements disposed circumferentially about the engagement portion.

6. A surgical instrument as recited in claim 5, wherein at least one of the grooves includes a run-out including the arcuate surface.

7. A surgical instrument as recited in claim 1, wherein the at least one element engages the implant fastener to resist and/or prevent toggle therebetween.

8. A surgical instrument as recited in claim 1, wherein the engagement portion comprises splines.

9. A surgical instrument as recited in claim 1, wherein the member extends along the longitudinal axis between a proximal end and a distal end having an end surface, distal end including an opening that extends into the end surface, the opening being coaxial with the longitudinal axis.

10. A surgical instrument as recited in claim 1, wherein the engagement portion has a uniform diameter along an entire length of the engagement portion.

11. A surgical instrument as recited in claim 1, wherein the distal portion has a uniform diameter along entire lengths of the first sections.

12. A surgical instrument as recited in claim 1, wherein the proximal portion is tapered from the distal portion to the proximal tip.

13. A surgical instrument as recited in claim 1, wherein the proximal portion is tapered from the distal portion to the proximal tip to form a flute run-out.

14. A surgical instrument as recited in claim 1, wherein the at least one interference point is spaced apart from the proximal tip.

15. A surgical instrument as recited in claim 1, wherein the member extends along the longitudinal axis between a proximal end and a distal end having an end surface, the groove comprising a distal opening extending through the end surface.

16. A surgical instrument as recited in claim 1, further comprising the implant fastener, wherein the implant fastener includes an inner surface defining a socket configured for mating engagement with the engagement portion, the inner surface including a protrusion configured for disposal within the groove, the proximal tip being positioned outside of the socket when the protrusion is disposed within the groove.

17. A surgical instrument comprising:
a driver defining a longitudinal axis and including a self-retaining engagement portion, the engagement portion including a plurality of lobes defining grooves therebetween engageable with an implant fastener, each of the lobes including a drive edge and a trailing edge, the drive edge and the trailing edge defining a groove therebetween, the drive edge intersecting the trailing edge at a proximal tip of the groove, wherein the groove includes a distal portion defined by a first section of the drive edge and a first section of the trailing edge and a proximal portion defined by a second section of the drive edge and a second section of the trailing edge, wherein the first section of the drive edge, the first section of the trailing edge and the second section of the drive edge each extend parallel to the longitudinal axis, wherein the second section of the trailing edge is arcuately curved from the first section of the trailing edge to the proximal tip, and wherein the drive edges define maximum lengths of the lobes, the second section of the trailing edge including at least one interference point engageable with the implant fastener to resist and/or prevent toggle therebetween.

18. A surgical instrument as recited in claim 17, wherein each of the grooves includes a run-out.

19. A surgical instrument as recited in claim 17, wherein the lobes are disposed circumferentially about the engagement portion.

20. A surgical instrument comprising:
a member comprising a shaft defining a longitudinal axis, an end of the shaft including an engagement portion, the engagement portion including at least one element engageable with an implant fastener, the at least one element including a drive edge and a trailing edge, the drive edge and the trailing edge defining a groove therebetween, the drive edge intersecting the trailing edge at a proximal tip of the groove, wherein the groove includes a distal portion defined by a first section of the drive edge and a first section of the trailing edge and a proximal portion defined by a second section of the drive edge and a second section of the trailing edge, wherein the first section of the drive edge, the first section of the trailing edge and the second section of the drive edge each extend parallel to the longitudinal axis, wherein the second section of the trailing edge is arcuately curved from the first section of the trailing edge to the proximal tip, and wherein the engagement portion has a uniform diameter along an entire length of the engagement portion.

* * * * *